United States Patent [19]

Knochel et al.

[11] Patent Number: 4,946,618

[45] Date of Patent: Aug. 7, 1990

[54] TOILET BAR COMPOSITION CONTAINING CATIONIC GUAR GUM

[75] Inventors: John R. Knochel; Paul E. Vest, both of Cincinnati, Ohio

[73] Assignee: The Procter & Gamble Company, Cincinnati, Ohio

[21] Appl. No.: 456,065

[22] Filed: Dec. 21, 1989

Related U.S. Application Data

[63] Continuation of Ser. No. 266,039, Nov. 2, 1988, abandoned.

[51] Int. Cl.$^5$ .................. C11D 9/30; C11D 13/18
[52] U.S. Cl. .................. 252/117; 252/108; 252/121; 252/132; 252/134; 252/174.23; 252/174.17; 252/DIG. 16
[58] Field of Search .............. 252/117, 132, 547, 134, 252/DIG. 16, 174.17, 174.23, 121, 108

[56] References Cited

U.S. PATENT DOCUMENTS

| | | | |
|---|---|---|---|
| 3,761,418 | 9/1973 | Parran, Jr. | 252/106 |
| 4,012,341 | 3/1977 | Orshitzer et al. | |
| 4,234,464 | 11/1980 | Morshauser | 252/545 |
| 4,491,539 | 1/1985 | Hoskins et al. | 252/541 |
| 4,704,224 | 11/1987 | Saud | 252/132 |
| 4,820,447 | 4/1989 | Medcalf et al. | 252/117 |

FOREIGN PATENT DOCUMENTS

| | | |
|---|---|---|
| SHO 57-105500 | of 1982 | Japan . |
| SHO 58-23900 | of 1983 | Japan . |
| SHO 58-167700 | of 1983 | Japan . |
| 1314604 | 4/1970 | United Kingdom . |
| GB 2094307A | 9/1982 | United Kingdom . |
| GB 2114994A | 9/1983 | United Kingdom . |
| GB 2103236A | 2/1984 | United Kingdom . |

OTHER PUBLICATIONS

Cosmetics & Toiletries, vol. 99, Jun. 1984, pp. 83–87, "Cationic Guar Gum".
"Polymer Jr. for Skin Care", by Union Carbide, 1977.
Polymers for Personal Care Products, Jaguar C-14-S, Celanese Corp., 3/85.
Polymers for Personal Care Products, Jaguar C-15, Celanese Corp., 4/85.
"What is Jaguar?", pp. 5–31, 1985, Celanese Polymer Specialties Co.
Product Data Bulletins re: Jaguar C-13-S and Jaguar HP-60, 1985, Celanese Polymer Specialties Co.

Primary Examiner—Prince E. Willis
Attorney, Agent, or Firm—Leonard Williamson; Robert B. Aylor; Richard C. Witte

[57] ABSTRACT

Toilet bar compositions containing alkali metal soap and cationic guar gum provided by a fast hydrating cationic guar gum. The bars exhibit improved bar feel. The formulations of the bars have improved processability. The toilet bars comprise alkali metal soap and from about 0.2% to about 5% by weight of the fast hydrating cationic guar gum.

11 Claims, No Drawings

TOILET BAR COMPOSITION CONTAINING CATIONIC GUAR GUM

This is a continuation of application Ser. No. 07/266,039, filed on Nov. 2, 1988, now abandoned.

FIELD OF THE INVENTION

This invention pertains to personal cleansing toilet bar compositions for personal washing, which compositions comprise cationic guar gum.

| U.S. Patent Documents | | | |
|---|---|---|---|
| U.S. Pat. No. | Date | Inventor(s) | U.S. Class/Sub. |
| 3,761,418 | 9/1973 | Parran, Jr. | 252/106 |
| 4,234,464 | 11/1980 | Morshauser | 252/544 |
| 4,061,602 | 12/1977 | Oberstar et al. | 252/547 |
| 4,472,297 | 9/1984 | Bolich et al. | 252/531 |
| 4,491,539 | 1/1985 | Hoskens et al. | 252/541 |
| 4,540,507 | 9/1985 | Grallier | 252/174.23 |
| 4,673,525 | 6/1987 | Small et al. | 252/132 |
| 4,704,224 | 11/1987 | Saud | 252/132 |
| Other Documents | | | |
| Jap. J57105 | 6/30/82 | Pola | |

Cosmetics & Toiletries, Vol. 99, June 1984, pp. 83-87, Allured Publishing Co., "Cationic Guar Gum," by Freeland et al.

BACKGROUND OF THE INVENTION

Toilet bars based on soap (alkali metal salts of fatty acids) are commonly used for cleansing the human body. A wide variety of additives have been suggested for inclusion in toilet bars. Some enhance the physical properties of the bar (hardness, wear rate, resistance to water). Others enhance the in-use properties of the toilet bar (lather characteristics such as volume and texture), and some impact on the impression the bar has on the skin both during washing (bar feel) and afterwards.

Polymeric Skin Mildness Aids

It has been discovered that the addition of certain polymeric materials to toilet bars can have a beneficial skin mildness effect for the user without deleteriously affecting other bar properties. On the other hand, some polymeric materials are very difficult to incorporate into bars and result in a gritty in-use skin feel. In general, the useful polymers should be soluble or dispersible in water to a level of at least 1% by weight, preferably at least 5% by weight at 25° C. Suitable polymers are high molecular weight materials (mass-average molecular weight determined, for instance, by light scattering, being generally from about 20,000 to about 5,000,000, preferably from about 50,000 to about 4,000,000, and more preferably from about 500,000 to about 3,000,000) and preferably have a thickening ability such that a 1% dispersion of the polymer in water at 20° C. exceeds about 1 PaS (10 poise) at a shear rate of $10^{-2} \sec^{-1}$. Useful polymers are the cationic, nonionic, amphoteric, and anionic polymers useful in the cosmetic field. Preferred are cationic and nonionic resins and mixtures thereof. Highly preferred are the cationic resins. The level of polymer is from about 0.01% to about 5%, preferably from about 0.1% to about 2%. (Unless otherwise specified, all percentages in this specification are percentages by weight.) Nonionic polymers include guar gum and hydroxypropyl guar gum.

Preferred are the cationic polymers which include cationic guar gums such as hydroxyproxyltrimethylammonium guar gum such as that available commercially under the trademarks Jaguar C-17 and Jaguar C-15 as marketed by Hi-Tek Polymers of Louisville, Ky.

The Problem

The problem with using prior art slow hydrating cationic guar gums in soap bars is that they present costly processing problems and often result in gritty feeling bars. The use of prior art slow hydrating cationic guar gums to dried soap flakes, i.e., at the milling step, results in inconsistent and unacceptable bar feel. Commonly assigned U.S. patent application Ser. No. 119,284, Medcalf, Jr., Visscher, Knochel and Dahlgren, filed Oct. 30, 1987, now U.S. Pat. No. 4,820,447, issued Apr. 11, 1989, discloses a soap bar comprising hydrated cationic guar gum, incorporated herein by reference. Medcalf, Jr., et al., addressed this serious gritty feeling problem associated with making soap bars using cationic guar gum. Medcalf, Jr., et al. teaches that the gritty feeling problem is solved by insuring that the cationic guar gum is hydrated and well incorporated into the soap bar matrix. However, the cationic guar gums specifically disclosed in Medcalf, Jr., et al., if added to dried soap flakes, do not hydrate rapidly enough to avoid the gritty feeling problem.

SUMMARY OF THE INVENTION

The present invention relates to a toilet bar made with a fast hydrating cationic guar gum. In another respect, the present invention relates to a process for making a soap bar involving adding dry, fast hydrating cationic guar gum to dried soap flakes at the mixing/milling step of a conventional soap bar making process.

OBJECTS OF THE INVENTION

An object of the present invention is to provide an improved process for adding a cationic guar gum skin conditioning agent to soap bar formulations.

Other objects will become apparent from the detailed description below.

DETAILED DESCRIPTION OF THE INVENTION

The present invention comprises a soap bar composition comprising from about 0.2% to about 5% by weight cationic guar gum, said guar gum being provided by fast hydrating cationic guar gum added as a dry powder or a dispersed powder to dried soap noodles at the mixing/milling step of a conventional soap bar making process. Compared to toilet bars which are prepared with slow hydrating cationic guar gum added dry to soap flakes at the mixing/milling steps, the toilet bars of this invention consistently exhibit superior bar feel due to the fast hydrating cationic guar gum. A fast hydrating cationic guar gum is defined herein as one which at a level of 2.6% guar has a viscosity of at least about 500 cps, preferably about 800 cps, in a 9.5% alkaline salt (pH 9.4) solution at 38° C. in about 10 minutes. Another definition of a fast hydrating cationic guar gum is one that can be uniformly incorporated into dried soap flakes at the mixing/milling step.

The Soap Component

The soap component of the present compositions preferably comprises from about 50% to about 90% by weight alkali metal soap (anhydrous basis) and is an alkali metal (e.g., sodium or potassium) soap or mixture of soaps of fatty acids containing from about 8 to about 24, preferably from about 10 to about 20 carbon atoms. The fatty acids used in making the soaps can be obtained from natural sources such as, for instance, plant or animal-derived glycerides (e.g., palm oil, coconut oil, babassu oil, soybean oil, castor oil, whale oil, fish oil, tallow, grease, etc., and mixtures thereof. The fatty acids can also be synthetically prepared (e.g., by oxidation of petroleum stocks by the Fischer-Tropsch process).

Alkali metal soaps can be made by direct saponification of the fats and oils or by the neutralization of the free fatty acids which are prepared in a separate manufacturing process. Particularly useful are the sodium and potassium salts of the mixtures of fatty acids derived from coconut oil and tallow, i.e., sodium and potassium tallow and coconut soaps.

The term "tallow" is used herein in connection with fatty acid mixtures which typically have an approximate carbon chain length distribution of 2.5% $C_{14}$, 29% $C_{16}$, 23% $C_{18}$, 2% palmitoleic, 41.5% oleic and 3% linoleic. (The first three fatty acids listed are saturated.) Other mixtures with similar distribution, such as the fatty acids derived from various animal tallows and lard, are also included within the term tallow. The tallow can also be hardened (i.e., hydrogenated) to convert part or all of the unsaturated fatty acid moieties to saturated fatty acid moieties.

When the terms "coconut oil" and "coconut fatty acid" (CNFA) are used herein, they refer to fatty acid mixtures which typically have an approximate carbon chain length distribution of about 8% $C_7$, 7% $C_{10}$, 48% $C_{12}$, 17% $C_{14}$, 9% $C_{16}$, 2% $C_{18}$, 7% oleic, and 2% linoleic. (The first six fatty acids listed are saturated.) Other sources having similar carbon chain length distribution such as palm kernel oil and babassu kernel oil are included with the terms coconut oil and coconut fatty acid.

In the compositions of the present invention, the soap component is preferably either sodium soap or a mixture of sodium and potassium soap wherein the mixture contains no more than about 25% by weight potassium soap.

Also, it is preferable in such bars that the total soap component comprises (a) from about 20% to about 80% by weight of the soap component of a mixture containing soaps having from 8 to 14 carbon atoms and (b) from about 20% to about 80% by weight of the soap component of soaps having from about 16 to about 20 carbon atoms.

Soaps having such preferred chain length distribution characteristics can be realized by utilizing mixtures of tallow and coconut fatty acids in tallow/coconut weight ratios varying between 90:10 and 50:50. A mixture of soaps of tallow and coconut fatty acids in the tallow/coconut weight ratio of 80:20 is especially preferred. A preferred soap bar of this invention also comprises from at least 25% of tallow soap. Another preferred bar of this invention comprises a 50/80% T/CN fatty acid soap mixture.

A preferred soap bar of this invention comprises about 50% soap as its primary or sole surfactant It also contains as an essential ingredient a skin conditioning amount of a hydrated, cationic guar gum provided by a "fast hydrating" cationic guar gum polymer. This polymer is uniformly distributed in the soap bar matrix without affecting the smooth feel of the dry or wet bar and improves the skin feel of the bar when compared to a comparably processed soap bar with a slow hydrating guar gum polymer. The mildness achieved approaches that of toilet bars based on mild synthetic surfactants as disclosed in commonly assigned U.S. Pat. No. 4,673,525, Small et al., issued June 16, 1987, incorporated herein by reference. Yet the preferred bar of this invention maintains the highly acceptable physical and in-use characteristics of a pure soap bar.

Synthetic Detergents

Synthetic detergents can also be present in compositions herein. Preferred types of synthetic detergents are of the anionic or nonionic type. Examples of anionic synthetic detergents are the salts of organic sulfuric reaction products such as alkyl sulfates having the formula $R_{24}OSO_3M$;
alkyl sulfonates having the formula $R_{24}SO_3M$;
alkyl ether sulfates having the formula $R_{24}(OC_2H_4)_xOSO_3M$;
alkyl mono glyceride sulfonates having the formula

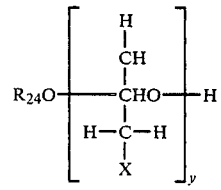

and alkyl benzene sulfonates having the formula

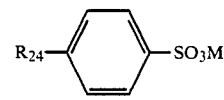

In the above formulae, $R_{24}$ is a straight or branched chain alkyl of from about 8 to about 24 carbon atoms; M is an alkali metal or ammonium ion; x is a number of from 1 to about 10; y is a number of from 1 to 4; and X is selected from the group consisting of chlorine, hydroxyl, and $-SO_3M$, at least one X in each molecule being $-SO_3M$. Examples of nonionic synthetic detergents are ethoxylated fatty alcohols (e.g., the reaction product of one mole of coconut fatty alcohol with from about 3 to about 30 moles of ethylene oxide) and fatty acid amides such as coconut fatty acid monoethanolamide and stearic acid diethanolamide. Although it may be desirable in some instances to incorporate synthetic detergents into the compositions of the present invention, the compositions herein can be free of synthetic detergents. Preferred are the mild synthetic surfactants disclosed in U.S. Pat. No. 4,673,525, Small et al., issued June 16, 1987, incorporated herein by reference.

Insoluble Alkaline Earth Metal Soaps

Insoluble alkaline earth metal soaps such as calcium stearate and magnesium stearate can also be incorporated into compositions of the present invention at levels up to about 30%. These materials are particularly useful in toilet bars in which synthetic detergents are present in that they tend to reduce the relatively high solubility which such bars normally have. These alkaline earth metal soaps are not included within the term "soap" as otherwise used in this specification. The terms "soap" as used herein refers to the alkali metal soaps.

The Fast Hydrating Cationic Guar Gum

Powdered or dispersed fast hydrating cationic guar gum polymer is hydrated and uniformly dispersed and incorporated into the soap bar formulation by mixing same with dried soap flakes, i.e., at the mixing/milling step.

The soap bar of this invention comprises about 0.2% to 5%, preferably 0.5% to 2%, of the fast hydrating cationic guar gum polymer. The molecular weight of the preferred cationic guar gum is from about 50,000 to about 1,000,000, preferably from about 100,000 to about 500,000, and more preferably from about 250,000 to about 400,000. Other cationic polymeric skin conditioners can also be used.

The essential component of the toilet bar of the present invention is the fast hydrating cationic guar gum. The term "fast hydrating cationic guar gum" is defined herein as a 2.6% polymer which has a viscosity of at least about 500 cps, preferably at least about 800 cps, in about 10 minutes in a 9.5% alkaline (pH 9.4) salt (NaCl) water at 38° C., preferably at least 1000 cps in 30 minutes. The preferred guar gum has a viscosity profile of:
from 5 to 500 cps in 5 minutes;
from 1,000 to 5,000 cps in 30 minutes;
from 3,000 to 9,000 cps in 60 minutes; and
from 5,000 to 14,000 cps in 120 minutes.

Guar gum is a natural material derived from ground up endosperms of *Cyamopsis tetragonolobus.* Preferably, the guar gum used in the present invention is a free flowing powder having a particle size on a 150 mesh of from 0% to about 10%, preferably from about 3% to about 5% maximum and through a 250 mesh of at least 50%, preferably at least 65%.

The fast hydrating cationic guar gum is incorporated into the soap composition of this invention (as described below) at a level of from about 0.2% to about 5%, preferably from about 0.5% to about 4%. The guar gum is surprisingly hydrated as it is introduced into the composition at the mixing/milling step of a conventional soap making process. Preferably, the composition comprises from about 0.5% to about 3% guar gum, more preferably from about 1% to about 2%.

TABLE

Cationic Jaguar Guar Gum Viscosities

| Jaguar Codes | Viscosity cps* | | | |
|---|---|---|---|---|
| | 5 min. | 30 min. | 60 min. | 120 |
| 375 FA RMS | 100 | 2100 | 4200 | 5500 |
| 376 FA | 100 to 700 | 2150 to 5300 | 4400 to 9460 | 5600 to 12,000 |
| 376 (slow) | 15–20 | 75–170 | 215–420 | 560–1300 |
| C15AW RMS | 100 | 500 1500 | 2000 | |
| C15AW (fast) | 210 to 920 | 1000 to 2300 | 1800 to 3600 | 2600 to 4400 |
| C15AW (slow) | 15 | 100 | 200 | 540 |

*The rate of hydration is defined in terms of the viscosity of a 2.6% guar gum polymer in a 9.5% NaCl alkaline (9.4 pH) water solution at 38°° C.

A preferred fast hydrating cationic guar gum is Jaguar C376FA made by Hi-Tek Polymers, Inc., Louisville, Ky. Jaguar C376FA has a viscosity of at least about 2000 cps in 30 minutes in the 2.6% cationic guar gum polymer/alkaline/salt water solution at 38° C.

Water Content

However, some toilet bars comprising a substantial amount of synthetic surfactant as its primary surfactant can contain as little as from 3.5% to 4.5% water. The toilet bars generally contain from about 8% to about 20% water.

Optional Components

The toilet bar compositions of the present invention can contain optional components such as those conventionally found in toilet bars. Conventional antibacterial agents can be included in the present compositions at levels of from about 0.5% to about 4%. Typical antibacterial agents which are suitable for use herein are 3,4-di and 3,4',5-tribromosalicyla-anildes; 4,4'-dichloro-3-(trifluoromethyl)carbanilide; 3,4,4'-trichlorocarbanilide and mixtures of these materials. Conventional nonionic emollients can be included as additional skin conditioning agents in the compositions of the present invention at levels up to about 40%, preferably at levels of from about 1% to about 25%. Such materials include, for example, mineral oils, paraffin wax having a melting point of from about 100° F., fatty sorbitan esters (see U.S. Pat. No. 3,988,255, Seiden, issued Oct. 26, 1976, incorporated by reference herein), lanolin and lanolin derivatives, esters such as isopropyl myristate and triglycerides such as coconut oil or hydrogenated tallow.

Free fatty acid such as coconut fatty acid can be added to the compositions herein to improve the volume and quality (creaminess) of the lather produced by the compositions herein.

Conventional perfumes, dyes and pigments can also be incorporated into compositions of the invention at levels up to about 5%. Perfumes are preferably used at levels of from about 0.5% to 3% and dyes and pigments are preferably used at levels of from about 0.001% to about 0.5%.

Bar Preparation

Toilet bars of the present invention can be prepared in the conventional manner. Powdered, fast hydrating cationic guar gum is added to noodles of the base soap mixture containing from about 10% to about 22% moisture in an amalgamator. Any optional ingredients such as perfumes, dyes, etc., are also added to the amalgamator. The mixture is processed in the amalgamator and milled in the conventional manner under conventional conditions. It is then extruded (plodded) into logs for cutting and stamping into toilet bars.

In a method of making the bar of the present invention, the guar gum cationic polymer is hydrated with the moisture in the soap noodle mix in the soap mixing steps of the soap bar making process. Hydration of the polymer is fast. The fast hydrating polymer goes into the soap mixture readily and the polymer is distributed uniformly without significant numbers of nonhydrated polymer chunks. The uniform distribution of the polymer maintains highly acceptable soap bar feel in-use characteristics.

The soap bars of this invention preferably contain up to 20% of a synthetic surfactant. If a synthetic surfactant is included, a mild one is preferred. A mild synthetic surfactant is defined herein as one which does relatively little damage to the barrier function of the stratum corneum. The mild surfactant is preferably used at a level of 0-20%, preferably about 2-15%. The fatty acid soap and mild surfactant mixture preferably has a ratio of 2.5:1 to 37:1, preferably from 2.5:1 to 14:1, and most preferably from 6.5:1 to 14:1, soap:synthetic.

A preferred soap bar of this invention also contains from about 2% to about 17% moisturizer, preferably one selected from glycerin and free fatty acid or mixtures thereof. The more preferred bar of this invention contains at least 4% moisturizer.

Some preferred mild synthetic surfactants useful in this invention include alkyl glyceryl ether sulfonate (AGS), anionic acyl sarcosinates, methyl acyl taurates, N-acyl glutamates, alkyl glucosides, acyl isethionates, alkyl sulfosuccinate, alkyl phosphate esters, ethoxylated alkyl phosphate esters, alkyl ether sulfates, methyl glucose esters, protein condensates, mixtures of alkyl ether sulfates and alkyl amine oxides, betaines, sultaines, and mixtures thereof. Included in the surfactants are the alkyl ether sulfates with 1 to 12 ethoxy groups, especially ammonium and sodium lauryl ether sulfates. Alkyl chain lengths for these surfactants are $C_8$–$C_{22}$, preferably $C_{10}$–$C_{18}$. The most preferred mild surfactant is sodium CN AGS.

Other Cationic Polymers

Other cationic polymeric skin conditioning agents useful in the present invention have molecular weights of from 1,000 to 3,000,000 and are selected from the group consisting of:
(I) other cationic polysaccharides;
(II) cationic copolymers of saccharides and synthetic cationic monomers, and
(III) synthetic polymers selected from the group consisting of:
  (A) cationic polyalkylene imines
  (B) cationic ethoxy polyalkylene imines, and
  (C) cationic poly[N-[-3-(dimethylammonio)propyl]-N'-[3-(ethyleneoxyethylene dimethylammonio)propyl]urea dichloride].

Specific examples of members of the cationic polysaccharide class include the cationic hydroxyethyl cellulose JR-400 made by Union Carbide Corporation; the cationic starches Stalok ® 100, 200, 300 and 400 made by Staley, Inc.

The cationic copolymers of saccharides and synthetic cationic monomers useful in the present invention encompass those containing the following saccharides: glucose, galactose, mannose, arabinose, xylose, fucose, fructose, glucosamine, galactosamine, glucuronic acid, galacturonic acid, and 5 or 6 membered ring polyalcohols. Also included are hydroxymethyl, hydroxyethyl and hydroxypropyl derivatives of the above sugars. When saccharides are bonded to each other in the copolymers, they may be bonded via any of several arrangements, such as 1,4-α; 1,4,-β; 1,3-α; 1,3-β and 1,6 linkages. The synthetic cationic monomers for use in these copolymers can include dimethyldiallylammonium chloride, dimethylaminoethylmethyacrylate, acrylamide, diethyldiallylammonium chloride, N,N-diallyl,N-dialkyl ammonium halides, and the like.

Examples of members of the class of copolymers of saccharides and synthetic cationic monomers include those composed of cellulose derivatives (e.g., hydroxyethyl cellulose) and N,N-diallyl,N-N-dialkyl ammonium chloride available from National Starch Corporation under the trade name Celquat.

The cationic synthetic polymers useful in the present invention are cationic polyalkylene imines, ethoxypolyalkylene imines, and poly[N-[-3-(dimethylammonio)propyl]-N'-[3-(ethylene-oxyethylene dimethylammonio)propyl]urea dichloride]the latter of which is available from Miranol Chemical Company, Inc. under the trademark of Miranol A-15, CAS Reg. No. 68555-36-2.

It is noteworthy that the cationic guar gums JAGUAR C-14-S and C-15 are purposely designed by the supplier to hydrate slowly. This slow hydration feature is believed to be necessary for the typical uses of these guar materials in shampoos and conditioners, where premature hydration and subsequent viscosity growth are detrimental to such formulation process.

Visual Tactile Evaluations

Hydration of the cationic guar gum polymer can be judged during the soap making process by examination of the soap mix after the polymer has been added and mixed for at least 10 minutes. It is preferred that no lumps of polymer be visible to the eye during this examination. Additionally, the feel of the resultant test soap mix must not be gritty or grainy upon evaluation in water. On a scale of 0 to 10, the bar should be 7 or better.

The following examples are presented by way of illustration only.

EXAMPLE I

In general, procedures common to conventional toilet soap bar making are employed.

Continuous Crutching Step

About 120.1 parts of a mix containing 29.4% moisture, 54.5% 50/50 tallow/coconut soap (T/CN), 7.3% CN alkyl glycerol sulfonate (AGS), 3.3% glycerin, 0.7% NaCl, and approximately 1.5% miscellaneous are mixed in line. The mix temperature is approximately 150°–200° F. (65°–94° C.).

Vacuum Drying and Plodding Steps

The mix is vacuum dried at about 50 mm Hg absolute pressure to reduce its moisture to approximately 11%. The resultant dried soap is plodded into noodles.

Mixing/Milling Steps

Polymer Addition Step

The plodded noodles are conveyed to a continuous mixer (CM) where approximately 1.0 parts each of Jaguar C-376FA and Merquat 550 polymers are introduced, mixed, and plodded with the soap noodles. Uniform distribution during this addition and mixing step and the absence of any liquid flows, especially glycerin, are important for acceptable bar feel performance. The polymer/soap noodles (generic noodles) are conveyed to milling.

Generic Milling Step

Two four-roll soap mills (feed, stationary, middle, top rolls) are used in this step. This is a split milling (two set of mills are used in parallel) process to obtain an homogeneous mix. Efficient milling is needed in this intimate mixing step.

Dry Mixing Step

The generic noodles are conveyed to a second process system continuous mixer (CM) for the addition and mixing of 1.5 parts of trichlorocarbanilide (TCC) and 0.24–0.55 parts of $TiO_2$. This mix is plodded and conveyed to the third process CM.

Wet Mixing Step 1.2 parts of perfume, 1.1 parts of NaCl/diethylene triamine acetate (DTPA) solution, and 0.0 to 0.50 parts of color solution are added and mixed in this web mixing (CM) step. This finished soap formula is then plodded into soap noodles and conveyed via a transport plodder to a final milling step.

The mixture is milled using a four-roll mill, plodded, and then stamped into toilet bars of any convenient size and shape. The resulting bars demonstrate enhanced physical properties particularly good, bar feel properties and the skin mildness mentioned above.

EXAMPLES II-VII

Toilet bars are prepared using the process of Example I, except that the cationic guar gums as set out in Table 2 are used. Their viscosity profiles are set out in Table 1.

TABLE 2

| Example | Jaguar | Bar Feel |
|---|---|---|
| II | 376FA RMS (fast) | Excellent |
| III | 376FA (fast) | Excellent |
| IV | 376 (slow) | Very Poor |
| V | C15AW RMS (slow) | Poor |
| VI | C15AW (fast) | Good |
| VII | C15AW (slow) | Poor |

Note that the bars of the present invention containing the fast hydrating cationic guar gums have much better bar feels than the slow hydrating guar gums.

Compared to toilet bars which are prepared with slow hydrating cationic guar gum added dry to dried soap noodles or flakes at the mixing/milling steps of a conventional bar soap making process, the toilet bars of this invention consistently exhibit superior bar feel due to the fast hydrating cationic guar gum.

What is claimed is:

1. A process for preparing toilet bars comprising the steps of:
    (a) forming a mixture of fast hydrating cationic guar gum and alkali metal soap mix noodles wherein said guar gum is present in said mixture at a level of from about 0.2% to about 5% by weight of said mixture; said mixture containing from about 6% to about 15% moisture;
    (b) hydrating said fast hydrating guar gum by forming a uniform mixture of (a);
    (c) extruding said uniform mixture; and
    (d) stamping said extruded mixture into said toilet bars; and
wherein said fast hydrating cationic guar gum at a level of 2.6% has a viscosity of at least about 500 cps in about 10 minutes in a 9 5% alkaline (pH 9.4) salt (NaCl) water solution at 38° C.

2. The process of claim 1 comprising from about 0.5% to about 4% cationic guar gum, wherein said viscosity is at least about 800 cps in about 10 minutes.

3. The process of claim 2 wherein said cationic guar gum is present at from about 1% to about 3% by weight of the bar.

4. The process of claim 1 wherein said cationic guar gum is present at from about 1% to about 2% by weight and wherein said viscosity is at least about 1,000 cps in about 30 minutes.

5. The process of claim 1 wherein said alkali metal soap comprises a mixture of alkali metal tallow soap and alkali metal coconut soap.

6. The process of claim 1 wherein said mixture of alkali metal tallow soap and alkali metal coconut soap comprises from about 1 to about 9 parts by weight alkali metal tallow soap per part by weight alkali metal coconut soap.

7. The process of claim 1 wherein said cationic guar gum has a viscosity profile of:
    from about 5 to about 500 cps in 5 minutes;
    from about 1,000 to about 5,000 cps in 30 minutes;
    from about 3,000 to about 9,000 cps in 60 minutes; and
    from about 5,000 to about 14,000 cps in 120 minutes.

8. The process composition of claim 1 wherein said composition contains from about 2% to about 20% of a synthetic surfactant selected from alkyl glyceryl ether sulfonates, anionic acyl sarcosinates, methyl acyl taurates, N-acyl glutamates, alkyl glucosides, acyl isethionates, alkyl sulfosuccinates, alkyl phosphate esters, ethoxylated alkyl phosphate esters, methyl glucose esters, protein condensates, mixtures of ethoxylated alkyl sulfates and alkyl amine oxides, betains, sultaines, the alkyl ether sulfates with 1 to 12 ethoxy groups, and mixtures thereof, wherein said synthetic surfactants contain $C_8$-$C_{22}$ alkyl chains.

9. The process of claim 1 wherein said composition contains up to 20% of a $C_{10}$-$C_{18}$ alkyl glyceryl ether sulfonate.

10. The process of claim 1 wherein said bar is dried to a moisture level of 7% to 15%.

11. A process of claim 1 wherein said moisture of Step (a) is from about 8% to about 12%.

* * * * *

UNITED STATES PATENT AND TRADEMARK OFFICE
CERTIFICATE OF CORRECTION

PATENT NO. : 4,946,618
DATED : August 7, 1990
INVENTOR(S) : JOHN R. KNOCHEL and PAUL E. VEST It is certified that error appears in the above-identified patent and that said Letters Patent is hereby corrected as shown below:

Col. 1, line 19, "Hoskens" should read -- Hoskins --.
Col. 1, line 20, "Grallier" should read -- Grollier --.
Col. 5, line 49 "120" should read -- 120 min. --.
Col. 5, line 54, "2000" should read -- 1500 --.
Col. 5, line 54, the blank in last column should read -- 2000 --.
Col. 5, line 55, "1500" should be deleted, it is listed in the wrong column and on wrong line.
Col. 10, line 27, (Claim 8) delete -- composition --.

Signed and Sealed this

Fourteenth Day of September, 1993

Attest:

BRUCE LEHMAN

*Attesting Officer*     *Commissioner of Patents and Trademarks*